United States Patent [19]

Coughlin et al.

[11] Patent Number: 5,173,413
[45] Date of Patent: Dec. 22, 1992

[54] ENHANCED BIOCONVERSION OF TOXIC SUBSTANCES

[76] Inventors: Robert W. Coughlin, 49 Storrs Heights Rd., Storrs, Conn. 06468; Wafaa M. Mahmoud; A. Halim El-Sayed, both of 133 Knollwood Dr., Wallingford, Conn. 06492

[21] Appl. No.: 663,328

[22] Filed: Feb. 28, 1991

[51] Int. Cl.[5] .......................... C12P 7/26; C12N 9/88; C12R 1/865
[52] U.S. Cl. .................................. 435/148; 435/232; 435/255; 435/940; 435/942
[58] Field of Search ............... 435/148, 940, 942, 232, 435/255

[56] References Cited

PUBLICATIONS

CA 13-76518(8) Mahmoud et al. (Bibiau) V36(1), p. 55-63 (1990).
CA 13-76519(9) Mohmoud et al. (Bibiau) V36(1), pp. 47-54 (1990).
BioTech Abs. 89-14950 Long et al. (Bibiau) V34, 7, pp. 933-941 (1989).
BioTech Abs. 90-10023 WO9004639 (Mar. 5, 1990).
Bar, Appl. Micro Biotech vol. 31, pp. 225-228 (1989).
Arcuri et al., Biotech & Bioeng. vol. 25; pp. 2399-2411 (1983).

*Primary Examiner*—Herbert J. Lilling

[57] ABSTRACT

Method and apparatus are provided for the bioconversion of toxic substrates with increased yields of product. The invention makes use of immobilized cells as biocatalyst and complexing agent in either dissolved or solid form. The invention also employs various schemes and apparatus for separating immobilized cells and complexing agent for recycle and re-use in bioconversion reactions. A preferred embodiment of the invention produces improved yields and titers of L-phenylacetyl carbinol by the bioconversion of acetaldehyde using yeast cells.

18 Claims, 1 Drawing Sheet

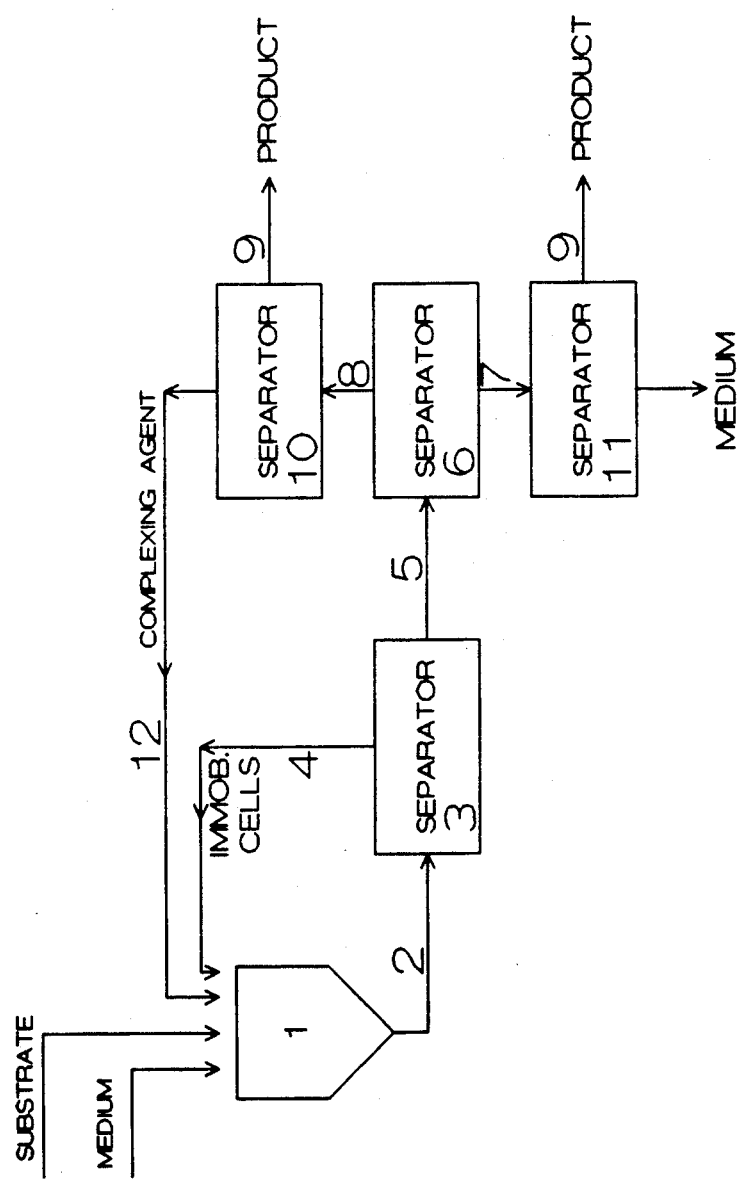

ENHANCED BIOCONVERSION OF TOXIC SUBSTANCES

BACKGROUND

1. Field of Invention

This invention relates to the chemical transformation of substances by living organisms, especially microorganisms. Products of such biotransformations range from foods such as yogurt and cheese to drugs such as steroidal hormones or drug intermediates such as L-phenylpropan-1-ol-2-one.

2. Discussion of Prior Art

All U.S. Patents cited herein are thereby incorporated herein by reference.

Production and accumulation of useful products formed by living organisms predates recorded history as in wine or beer production by fermentation. A comprehensive guide to compounds that are accumulated, produced, transformed or in some way acted upon by microorganisms and cell lines is *Microbes and Cells at Work*, published by American Type Culture Collection, Rockville, Md. (1988). Useful products so produced include antibiotics, amino acids, enzymes, organic fatty acids, nucleic acids, vaccines, vitamins, peptide hormones, steroid hormones, dextran and many other substances. A specific example is the use of *Aspergillus* species to transform progesterone to dihydroxyprogesterone.

Of specific interest for the present invention is the bioconversion of a substrate that is toxic to the living organism which brings about the biotransformation. Bioconversions of toxic substrates are very important in the treatment of toxic waste substances such as chlorinated hydrocarbons, pesticide residues such as organic phosphates or effluents from the manufacture of explosives such as dilute solutions of TNT or RDX which are very toxic compounds.

A specific case of biotransformation of a toxic substrate to a useful compound is the microbial biotransformation of benzaldehyde to L-1-ph-enylpropan-1-ol-2-one, frequently termed L-phenylacetyl carbinol and sometimes referred to herein as L-PAC. L-PAC is used as a raw material for the chemical synthesis of the drug ephedrine by a process described in U.S. Pat. No. 1,956,950 to Hildebrand and Klavehn (1934). Benzaldehyde is converted to L-PAC when added to a fermentation medium previously inoculated with yeast cell mass in the presence of fermentable sugar, a bioconversion reported as early as 1921 by Neuberg and Hirsch (Biochem Zeitschrift 115, 282-310) and Neuberg and Libermann, ibid 121, 311-339. See also Neuberg and Ohle ibid 127, 327-339 (1922) and 128, 610-618 (1922). The production of L-PAC from benzaldehyde by different species of yeast has been investigated by Gupta et al Biotechnol. & Bioeng. 21, 1085-89 (1979), Netrival et al [Eur. J. Appl. Microb. Biotech. 16, 35-38 (1982)] and Bringer-Meyer et al [Biocatalysis 1, 321 (1988)]. Gröger et al [Z. Für Allgem. Mikrobial. 6(4), 275-87 (1966)], Voets et al [Z. für Allgemm. Mikrobiol 13, 355-366 (1973)] and Agarwal et al [Biotechnol. and Bioeng. 29, 783-785 (1987) have investigated various processing methods and variables related to this bioprocess. Under normal fermentation conditions, quantitative conversion of benzaldehyde to L-PAC is never achieved, as reported by Smith et al [J. Bacterial 65, 440-45 (1953)] and Gupta et al (cited above).

The advantages of using immobilized cells for microbial biotransformation have been discussed by Arcuri et al [Biotechnol. & Bioeng. 25, 2399-2411 (1983)], Bihari et al [Biotechnol. & Bioeng. 26, 1403-08 (1984)], Scott [Enzyme & Microbial Tech. 9, 66-73 (1987)] and Fukui et al [Experientia 45, 1055-611 (1989)]. Fukui et al point out that a general disadvantage of immobilized living cells is undesirable metabolic activities which reduce product yields and increase permeability barriers for substrates and metabolites. Scott also cites the observation of Brodelius et al [Ann. N.Y. Acad. Sci. 434, 496-500 (1984)] that general microbial metabolism decreases upon immobilization, and the report of Robinson et al [Enzyme & Microbial Technology 7, 212–216 (1985)] that both respiration and growth rates of immobilized organisms decrease with increased cell concentration. Surprisingly, and in contrast to the findings of Fukui et al, Scott, Brodelins et al and Robinson et al we have found that immobilizing the yeast cells causes the yield of L-PAC from benzaldehyde to increase. In addition, we have also found that immobilization of the yeast cells also permits their exposure to higher concentrations of benzaldehyde while permitting higher productivity of L-PAC product from the biotransformation reaction. We hypothesize that immobilization may protect the yeast cells from toxic effects of the benzaldehyde substrate and perhaps also from toxic effects of the L-PAC product. This protection appears to occur in addition to the other well known favorable effects of cell immobilization, such as helping to maintain the cells in a bioreactor, facilitating the separation, recycling and re-use of the cells and protection of the cells from shear stress.

Bar [Appl. Microbiology and Biotechnology, 31, 225-28 (1989)] has reported that the presence of alpha-cyclodextrin (ACD) greatly enhances the conversion of benzylaldehyde to benzyl alcohol by yeast. Using an ACD concentration (27.5 g/L or 0.028 mols/l) which was greater than the molar equivalent of the benzaldehyde concentration (which was 3 g/L or 0.024 mol/L), Bar found that the yield of benzyl alcohol was increased to 67.4% (molar) after 24 hours, compared to only 15.4% (molar) in the absence of ACD.

The chemical equations representing the possible bioconversion reactions of benzaldehyde are:

      A.

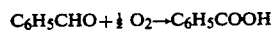      B.

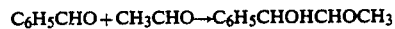      C.

As explained by Bringer-Meyer et al [Biocatalysis 1, 321-31 (1988)] acetaldehyde, which reacts with benzaldehyde to produce L-PAC according to reaction C above, is formed by the decomposition of pyruvate in yeast by pyruvate decarboxylase. It is evident that the greatly increased yield of benzyl alcohol to 67% (molar) by reaction A as observed by Bar must be associated with greatly reduced yield of L-PAC by reaction C, especially under anaerobic conditions. Thus Bar's disclosure shows that the use of ACD reduces the yield of L-PAC. Surprisingly, and in sharp contrast to Bar's findings, we have found that the inclusion of beta-cyclodextrin (hereinafter often referred to as BCD) in the fermentation medium greatly increases the yield of L-PAC. Also surprising is our discovery that substantial improvements in L-PAC yield are obtained using quantities of BCD far less than the molar amount of benzaldehyde substrate added to the fermentation medium. It appears that conducting the bioconversion of benzaldehyde in the presence of BCD may serve to protect the yeast cells from toxic effects of the substrate and perhaps also of the product. Whatever its mode of action, it is clear that the BCD has an additional favorable effect of increasing bioconversion selectivity to the product L-PAC, in contrast to the findings of Bar who observed that ACD increased the selectivity to benzyl alcohol.

Thus the present invention provides a bioprocess that has greatly improved economics over the prior art in that it facilitates higher yields of the valuable product L-PAC from a substrate such as benzaldehyde that is expensive as well as toxic to the biological transforming system.

OBJECTS AND ADVANTAGES

The present invention provides an improved microbial bioprocess and apparatus that permits higher yields of a product from biotransformation of a toxic substrate. The improved process of the present invention is achieved by the use of immobilized microbial cells and it thus combines all of the already known advantages of using immobilized cells with the previously unrecognized advantage of higher titers and yields of a product of biotransformation, as compared to the use of free cells. The present invention also provides a bioprocess of improved selectivity for a desired product from among a number of possible products that could be formed by biotransformation of a substrate such as benzaldehyde. The present invention provides the cited improvements by: (1) the use of immobilized microbial cells, (2) the use of a complexing agent such as BCD that is capable of forming complexes with a toxic substrate and (3) the combined use of immobilized cells and a complexing agent. Another object of the invention is to provide process and apparatus in which immobilized cells or complexing agent, or both cells and complexing agent, can be recovered for re-use after they are employed in biotransformation of a toxic substrate. Yet another object of the present invention is to permit higher concentrations of toxic substrate to be used in a biotransformation process, as compared to the prior art. A further object of the present invention is to provide process and apparatus for the selective bioconversion of benzaldehyde to L-PAC by the use of immobilized cells, or by the use of free cells together with a BCD complexing agent, or by the use of immobilized cells in combination with a BCD complexing agent. Yet another object is to provide method and apparatus that also accomplishes the recovery for re-use of immobilized cells and complexing agent in a process of biotransformation of a toxic substrate.

Further objects and advantages of the invention will become apparent from a consideration of the drawings and the description given below.

BRIEF DESCRIPTION OF THE FIGURE

FIG. 1 is a schematic flow diagram depicting the production and downstream separation of product produced by biotransformation of a toxic substrate according to the present invention.

DESCRIPTION OF THE INVENTION

According to the present invention, microbial cells are immobilized within a separate solid phase. The immobilized cells are held within a fermenter or bioreactor containing a liquid medium. A toxic substrate is fed to the fermenter wherein the desired biotransformation occurs by means of the immobilized biocatalyst. The cell immobilization permits better yields of desired products and permits the use of higher concentrations of toxic substrates. We hypothesize that immobilization may protect the cells from high concentrations of toxic substrate. However, the many possible effects of cell immobilization are poorly understood. The foregoing Scott reference and the Fukui et al reference describe many methods known in the art for immobilizing microbial cells for use in the present invention. Preferred methods of immobilization of microorganisms include entrapment within beads of alginate gel cross-linked by a divalent cation such as $Ca^{++}$, entrapment within a cross-linked polyacrylamide gel, or sorption within the pores of a solid carrier such as diatomaceous supports (e.g., Celites supplied by the Mannville Corporation, Denver, Colo., USA) or porous glass rings supplied by Schott and Mainz AG of Germany. Caunt and Chase [Biotechnology 6, 721-725 (1988)] have reported the use of bacteria immobilized on Celite for biodegradation. When porous solids are used for cell immobilization, it is often desirable to coat the solid carriers after immobilization with a layer of a cross-linked gel such as alginate, polyacrylamide, chitosan or a similar material. Preparation of such coated, immobilized-cell biocatalysts have been described by Mahmoud and Coughlin [Azhar J. Microbiol. 7, 1-15, (January 1990)]. An especially preferred embodiment of the present invention is to entrap cells of the yeast Saccharomyces cerevisiae within $Ca^{++}$-cross-linked alginate beads and use this immobilized biocatalyst for the transformation of the substrate benzaldehyde to the product L-PAC. Another embodiment is to use similarly immobilized pseudomonad bacteria or white-rot fungus to biotransform a hazardous substrate such as a chlorinated phenol to less hazardous products. For use in the present invention, cells can also be immobilized on cloth as disclosed by Yamazaki et al in U.S. Pat. No. 4,898,817 (February 1990).

In an embodiment of the present invention, a complexing agent is added to the fermentation medium before or during the addition of toxic substrate to the bioreactor. A complexing agent is a substance which combines under certain conditions with the toxic substrate to form therewith a complex or adduct that can dissociate reversibly to liberate or re-form the toxic substrate when conditions change. Preferred complexing agents include solid sorbents such as activated carbons, silica gels, zeolites, clays, solid ion exchange resins and porous solid polymers, or water-soluble substances such as chelating agents, ion exchangers such as organic sulfonates, clathrating agents, crown ethers, or any other agent that will form a host-guest or inclusion compound or other type of adduct with the toxic substrate. Examples of preferred soluble complexing agents are chitosans and cyclodextrins. Beta-cyclodextrin and its derivatives are especially preferred complexing agents in the present invention for use during biotransformation of benzaldehyde to L-PAC by yeast cells. According to an embodiment of the present invention, complexing agents are used during biotransformation of a toxic substrate either by free cells or by immobilized cells.

A preferred embodiment of the present invention employs immobilized cells and a complexing agent in the same bioreactor for the biotransformation of a toxic substrate. A preferred form of such an embodiment employs immobilized cells in the form of solid-gel beads or particles of average diameter in the range of about 1 mm to several mm and a complexing agent. A preferred form of complexing agent is a solid complexing agent in the form of particles of average diameter in the range of about 0.05 mm to about 0.95 mm. Alternatively, the solid complexing agent can be in the larger size range of about 1 mm to about several mm and the immobilized biocatalyst in the smaller size range of about 0.05 mm to about 0.95 mm. These two different size ranges facilitate the downstream separation of the products of biotransformation and the separate recycling and re-use of the immobilized cells and of the solid complexing agent. Another alternative is to immobilize the cells on a large, mesh structure such as the cloth used by Yamazaki et al cited above; the cloth-bound cells can then be retained in the reactor for re-use when the rest of the contents (medium + product + complexing agent) are withdrawn for recovery of product and separation, recycling and re-use of complexing agent.

When immobilized cells are used without complexing agent to biotransform a toxic substrate in the present invention, the liquid medium can be separated from the cells (e.g. by settling or by draining through a sieve) and the immobilized cells can be re-used for further biotransformation. The product of the biotransformation can be recovered from the liquid medium by precipitation, ion exchange, liquid extraction or by other methods well known in the art. In the case of production of L-PAC as disclosed herein, liquid extraction of L-PAC from aqueous medium into ether is a preferred recovery method. When a soluble complexing agent is used, in many cases the desired product may be combined with the complexing agent and the resulting adduct may precipitate thereby facilitating separation thereof, recovery of a desired product therefrom, and the recycling and re-use of the complexing agent. Separating cells (whether free or immobilized) from an adduct precipitate can be accomplished by differential settling (by gravity or by centrifugation) by differential filtration or by another liquid solid separation method known in the art. The separated cells can be re-used for additional biotransformation reaction. The adduct precipitate can be extracted with a solvent to recover the product as a solution in the solvent, leaving the complexing agent to be recycled and re-used for additional biotransformation reaction.

When a solid complexing agent is used with immobilized cells and the two types of solids are in different size ranges as stated above, then separation and recycling is greatly simplified as explained below with respect to operation, of an embodiment of the invention according to FIG. 1.

According to the present invention biotransformation of toxic substrate is conducted in an apparatus comprising a tank, vessel, container or reactor suitable for fermentation or chemical reaction. The tank or reactor contains particles of immobilized biocatalyst and liquid medium suitable for the biotransformation reaction. The apparatus is also equipped with conduit and valves as needed to feed substrate to the tank; a pump or gravity flow of substrate from a reservoir tank may be employed for feeding substrate. The apparatus also includes a suitable separation device such as a filter or sieve for separating biocatalyst particles from the medium after a bioconversion reaction so that the biocatalyst can be recovered and re-used for subsequent reaction. In many instances it will be useful to include a complexing agent such as BCD within the medium. An especially useful form of the complexing agent is that of solid particles in order to facilitate their separation from the liquid medium after the bioconversion so the particles can be recovered and re-used in subsequent bioconversions. In many instances it will be desirable for the solid complexing agent particles to have a different size range than the biocatalyst particles to facilitate downstream separation and re-use of the two different types of particles. A form of the apparatus for use with the two different types (and correspondingly different sizes) of particles includes two solid-liquid separators, one separator designed to remove the larger particles for re-use leaving a mixture of liquid medium and smaller particles, the other separator designed to separate the smaller particles from the mixture of smaller particles and liquid medium. When complexing agent, liquid medium and biocatalyst are separated from each other by suitable separators of the apparatus, it will often be desirable for the apparatus to include additional separators, such as liquid extraction units for extracting reaction product from the liquid medium, or for leaching reaction product from the separated solid complexing agent. The apparatus of the present invention also includes conduit or piping, valves, pumps, holding tanks and other ancillary components as may be needed for recovery, separation and recycling. If immobilized cells are in the form of sufficiently large particles or structures such as cloth, then the immobilized cells can be readily retained in the reactor when the liquid medium and complexing agent are removed therefrom; in such an instance, only a single liquid-solid separator is required to separate solid complexing agent from the liquid medium.

OPERATION OF A PREFERRED EMBODIMENT

Immobilized cells are placed in the bioreactor 1 of FIG. 1 together with suitable nutrient medium and solid complexing agent. Toxic substrate is also added thereto, either in a single dose or gradually over the course of time. The immobilized cells are in the form of beads about 1 mm to about 3 mm in diameter. The solid complexing agent is in the form of particles in the size range of about 0.05 mm to about 0.95 mm. The bioreactor is gently agitated by an impeller (not shown) or by a gas bubbled therethrough. Means for bubbling the gas are not shown in FIG. 1. The gas may be inert or it may contain oxygen for cell respiration as needed. After biotransformation of toxic substrate in reactor 1, the contents of the reactor are transferred by conduit 2 to liquid-solid separator 3 which can be a sieve or a filter of appropriate design to separate the larger beads of immobilized cells by retaining them, while permitting stream 5 of liquid reaction medium containing smaller particles of complexing agent to pass therethrough. The immobilized cells are recycled from separator 3 by conduit 4 to bioreactor 1 where they are re-used. If cells are immobilized on large supports or cloths which are easy to retain in the reactor, then separator 3 is not necessary. Provision can also be included for washing the immobilized cells before they are returned to the bioreactor but such washing components are not shown in FIG. 1. The other stream 5 from separator 3 passes to another separator 6 from which liquid medium (stream 7) is separated from solid complexing agent (stream 8), e.g. by filtration. The bioreaction product (stream 9) can then be recovered from solid complexing agent (stream 8), or from liquid medium (stream 7) by suitable separators 10 and 11. Many suitable separation methods for recovering a desired product are known in the art, e.g. liquid extraction from liquid medium or from solid complexing agent into a solvent. Thereafter, the solid complexing agent is returned (stream 12) for re-use to the bioreactor, and the liquid medium from separator 11 can be either re-used or discarded as a waste. In many cases, only one, but not both, of the separators 10 and 11 will be necessary. For example, if the product of the biotransformation forms a very stable adduct with the solid complexing agent then separator 10 is used. If the product is present only in the liquid medium, however, then only separator 11 may be used. If the product is present both in the liquid medium, and as an adduct with the solid complexing agent, then the separators 10 and 11 can be used.

An especially preferred embodiment of the present invention employs the processing scheme of FIG. 1 to bio-convert benzaldehyde to L-PAC using cells of the yeast Saccharomyces cerevisiac immobilized within $Ca^{++}$-crosslinked alginate beads. Preferred forms of solid complexing agent for use in this process are insolubilized BCD's produced by methods disclosed by Buckler et al in U.S. Pat. No. 3,472,835 (1969), Case in U.S. Pat. No. 3,510,471 (1970), Wiedenhof et al [Starch 21, 163 (1969, 23, 129 (1971)], Zsadon et al [Starch 31, 11 (1979)], Vretblad [FEBS Letters 47, 86 (1974)] and Philip et al [J. Food Sci. 50, 1205 (1985)]. Solid, insoluble BCD's can be obtained from Advanced Separation Technologies, Inc. Whippany, N.J. and American Maize-Products Company, Hammond, Ind.

EXAMPLES

EXAMPLE 1

(free cells)

Saccharomyces cerevisiae accession number ATCC 834 of the American Type Culture Collection, 12301 Parkland Drive, Rockville, Md., 20852 USA. was maintained on a medium that contained (per liter): 10 g of yeast extract, 10 g of malt extract, 4 g of dextrose, 20 g of agar. The liquid medium used for growing the yeast cells and for production of L-PAC contained (per liter): 6 g of yeast extract, 4 g of $(NH_4)SO_4$, 0.6 g of $MgSO_4$, 1 g of $KH_2PO_4$, 100 g of dextrose, with the balance water. For sterilization, a solution of dextrose and a solution containing the other ingredients were autoclaved separately, then mixed and the pH adjusted to 6.2. The yeast was grown for 24 hrs on the liquid medium at 28°–30° C., centrifuged, re-suspended in sterile water then re-centrifuged. Weighed amounts of wet cells were then used to inoculate free-cell fermentations conducted in 100 ml of medium in 250 ml Erlenmeyer flasks. The cell dose was 2.2 g (wet weight) in 100 ml of medium. After shaking under aerobic conditions for 1 hour, shaking was continued under anaerobic conditions. Pre-purified (by distillation) benzaldehyde was added in four equal aliquots at 1 hour intervals during the anaerobic shaking. The total amount of benzaldehyde added was 6 g per liter of medium. Thereafter, with continued shaking under anaerobic conditions, small samples were withdrawn over the ensuing 24-hour period and assayed for L-PAC by the method of Gröger et al (cited above). The maximum liter of L-PAC was 0.4 g/L.

EXAMPLE 2

(immobilized cells)

Example 1 was repeated, except that the washed and centrifuged cells were re-suspended in a solution containing 3% (w/v) of sodium alginate (Aldrich Chemical Company). The latter cell suspension was extruded as drops into a 2% calcium chloride solution thereby forming beads which were kept in the $CaCl_2$ solution for 1 hour before filtering and washing them on a Buchner funnel. These beads of immobilized yeast were then used to inoculate the medium in the shake flasks so that the cell dose was 1.3 g (cell wet weight) per 100 ml of medium. The procedure of Example 1 was then followed to produce L-PAC. The maximum titer of L-PAC found was 3.6 g/L.

EXAMPLE 3

(immobilized cells)

The procedure was identical to that of Example 2 except that the cell dosage was 2.8 g (wet weight) in 100 ml of medium. The maximum titer of L-PAC was 5.5 g/L.

EXAMPLE 4

(immobilized cells)

The procedure was identical to that of Example 2 except that the cell mass dose was 2.8 g (wet weight) per 100 ml of medium and the benzaldehyde dose was 8 g/L. The maximum titer of L-PAC formed was 3.5 g/L.

EXAMPLE 5

(immobilized cells)

The procedure was identical to that of Example 2 except that the cell mass dose was 2.8 g (wet weight) per 100 ml of medium and the benzaldehyde dose was 10 g/L. The maximum titer of L-PAC formed was 1.4 g/L.

The results of Examples 1–5 are collected together in the following Table:

| Example | Cell Dose g/L | Benzaldehyde Dose (g/L) | Maximum L-PAC Titer (g/L) | Type of Experiment |
|---|---|---|---|---|
| 1 | 22 | 6 | 0.4 | free cells |
| 2 | 13 | 6 | 3.6 | immobilized cells |
| 3 | 28 | 6 | 5.5 | immobilized cells |
| 4 | 28 | 8 | 3.5 | immobilized cells |
| 5 | 28 | 10 | 2.8 | immobilized cells |

The results of Examples 1–5 show the great superiority of using immobilized cells to achieve the selective production of L-PAC, as compared to free cells. Examples 3, 4 and 5 show that, even with immobilized cells, increasing doses of benzaldehyde produce reduced titers of L-PAC.

The following examples show the effects of adding BCD on the production of L-PAC.

EXAMPLES 6 AND 7

(immobilized cells)

Examples 6 and 7 were substantially identical to Example 3 except they were conducted with different cell masses and different benzaldehyde doses in a bubble column containing 100 ml of beads of immobilized cells and 400 ml of medium. During aerobic growth, air was gently bubbled up through the column to provide oxygen and agitation. During anaerobic bioconversion bubbled nitrogen provided the agitation. The results of Examples 6 and 7 are collected together with the results of Examples 8-11 in a table which follows Example 11.

EXAMPLES 8-11

(immobilized cells + BCD)

These were conducted substantially identically to Examples 6 and 7 except for different concentrations of BCD in the medium. The results are in the following table.

| Example | BCD Conc. % | Cell Dose g/L | Benz-aldehyde Dose (g/L) | Maximum L-PAC Titer (g/L) | Type of Experiment |
|---|---|---|---|---|---|
| 6 | 0 | 35 | 12 | 9 | immob. cells |
| 7 | 0 | 35 | 14 | 5 | immob. cells |
| 8 | 0.5 | 35 | 12 | 11 | immob. cells |
| 9 | 1.0 | 35 | 12 | 12 | immob. cells |
| 10 | 1.0 | 35 | 14 | 8 | immob. cells |
| 11 | 1.5 | 35 | 14 | 12 | immob. cells |

The foregoing Examples 6-11 indicate that the use of BCD greatly improves the selective yield of L-PAC from benzaldehyde.

Importantly and surprisingly, the addition of BCD permits the use of increasing doses of benzaldehyde without this causing decreased titers of L-PAC, an effect that is not seen with immobilized cells in the absence of BCD. This surprising, synergistic effect of cell immobilization combined with the use of BCD permits much higher production rates of L-PAC with a given apparatus and raw material charge, and is therefore of significant economic consequence. Another surprising aspect of the foregoing results is that the amounts of BCD employed were about only one tenth of the amounts equivalent to the benzaldehyde dosage on a molar basis.

RAMIFICATIONS AND SCOPE OF INVENTION

It is evident that the present invention provides improved method and apparatus for bioconversion of a toxic substrate to a useful, valuable product with improved yields and concentrations of the product in the medium. In an important embodiment it provides improved yields and concentrations of L-PAC as the product from bioconversion of benzaldehyde by yeast.

While the foregoing disclosure contains many specificities, these should not be construed as limitations on the scope of the invention, but rather as exemplifications of preferred embodiments thereof. For example, many different types of bioconversion reactions, cells, substrates, methods of immobilization, types of complexing agent and physical forms of complexing reagent can be employed in the present invention without departing from the spirit and scope thereof. Accordingly, the scope of the invention should be determined not by the embodiments illustrated, but by the appended claims and their legal equivalents.

We claim:

1. A method of converting benzaldehyde to phenylacetyl carbinol, by means of yeast, comprising the steps:
   a. maintaining said yeast in a medium comprising water and a complexing agent selected from the group consisting of beta cyclodextrin and derivatives thereof, said medium of a composition effective for supporting growth of said yeast and conversion by said yeast of benzaldehyde to phenylacetyl carbinol,
   b. feeding benzaldehyde to said yeast in said medium,
   c. recovering phenylacetyl carbinol produced by said conversion.

2. The method according to claim 1 wherein said medium contains a fermentable sugar.

3. The method according to claim 1 wherein said yeast is *Saccharomyces cerevisiae*.

4. The method according to claim 1 wherein said complexing agent is beta cyclodextrin.

5. The method according to claim 4 wherein said yeast is *Saccharomyces cerevisiae* and said medium contains a fermentable sugar.

6. The method according to claim 1 wherein said yeast is immobilized in the form of a solid biocatalyst.

7. The method according to claim 6 wherein said medium contains a fermentable sugar.

8. The method according to claim 6 wherein said complexing agent is beta cyclodextrin.

9. The method according to claim 6 wherein said yeast is *Saccharomyces cerevisiae*.

10. The method according to claim 7 wherein said complexing agent is beta cyclodextrin and said yeast is *Saccharomyces cerevisiae*.

11. The method according to claim 6 wherein said complexing agent is in the form of solid particles that are insoluble in said medium.

12. The method according to claim 11 wherein at least a portion of at least one member of the group consisting of said complexing agent and said solid biocatalyst is recovered and re-used for repeated conversion of benzaldehyde to phenylacetyl carbinol.

13. The method according to claim 11 wherein said solid biocatalyst is in the form of particles of a size range different from the size range of said solid particles of said complexing-agent and wherein recovery step c comprises the following steps:
   i. removal of at least a portion of the particles of the larger size range from said medium after said conversion, thereby producing a mixture comprising said medium and particles of the smaller size range,
   ii. removal of at least a portion of said particles of said smaller size range from said mixture from step i,
   iii. recovery of phenylacetyl carbinol from at least one member of the group consisting of said medium and said solid particles of said complexing agent,
   iv. recovering and re-using for conversion of benzaldehyde at least a portion of at least one member of the group consisting of said medium, said particles of said solid biocatalyst and said solid particles of said complexing-agent.

14. The method according to claim 1 wherein said complexing agent is in the form of solid particles that are insoluble in said medium.

15. The method according to claim 2 wherein said complexing agent is in the form of solid particles that are insoluble in said medium.

16. The method according to claim 3 wherein said complexing agent is in the form of solid particles that are insoluble in said medium.

17. The method according to claim 4 wherein said complexing agent is in the form of solid particles that are insoluble in said medium.

18. The method according to claim 5 wherein said complexing agent is in the form of solid particles that are insoluble in said medium.

* * * * *